United States Patent
Sunseri

(10) Patent No.: US 6,350,341 B1
(45) Date of Patent: Feb. 26, 2002

(54) NESTED TUBING SECTIONS AND METHOD FOR MAKING

(75) Inventor: Gary Sunseri, Hollister, CA (US)

(73) Assignee: Embol-X, Inc., Mountain View, CA (US)

( * ) Notice: Subject to any disclaimer, the term of this patent is extended or adjusted under 35 U.S.C. 154(b) by 0 days.

(21) Appl. No.: 09/350,780

(22) Filed: Jul. 9, 1999

Related U.S. Application Data

(62) Division of application No. 09/131,248, filed on Aug. 7, 1998, now Pat. No. 5,954,694.

(51) Int. Cl.⁷ ..................... A61M 29/00; B29C 65/02
(52) U.S. Cl. ...................... 156/253; 156/292; 156/294
(58) Field of Search ................. 156/294, 292, 156/253; 606/192, 194; 604/96.01, 103, 523, 264, 534

(56) References Cited

U.S. PATENT DOCUMENTS

| | | | |
|---|---|---|---|
| 3,288,901 A | * | 11/1966 | Clark |
| 3,613,684 A | * | 10/1971 | Sheridan |
| 3,834,394 A | | 9/1974 | Hunter et al. ............... 128/325 |
| 3,983,879 A | * | 10/1976 | Todd |
| 4,003,382 A | * | 1/1977 | Dyke |
| 4,285,341 A | | 8/1981 | Pollack ....................... 128/348 |
| 4,475,898 A | | 10/1984 | Brodner et al. ................ 604/9 |
| 4,582,181 A | | 4/1986 | Samson ................... 128/348.1 |
| 4,597,755 A | | 7/1986 | Samson et al. ............... 604/96 |
| 4,657,536 A | * | 4/1987 | Dorman |
| 4,668,225 A | | 5/1987 | Russo et al. ................ 604/270 |
| 4,777,951 A | | 10/1988 | Cribier et al. .............. 128/344 |
| 4,921,483 A | | 5/1990 | Wijay et al. ................... 604/96 |
| 4,961,731 A | | 10/1990 | Bodicky et al. ............. 604/264 |
| 4,961,809 A | * | 10/1990 | Martin |
| 5,021,045 A | * | 6/1991 | Buckberg et al. |
| 5,045,072 A | * | 9/1991 | Castillo et al. |
| 5,090,958 A | | 2/1992 | Sahota ......................... 604/98 |
| 5,183,470 A | | 2/1993 | Wettermann ................. 604/281 |
| 5,192,301 A | | 3/1993 | Kamiya et al. .............. 606/213 |
| 5,425,723 A | | 6/1995 | Wang .......................... 604/280 |
| 5,429,605 A | | 7/1995 | Richling et al. ............... 604/96 |
| 5,499,973 A | | 3/1996 | Saab ............................ 604/96 |
| 5,588,965 A | | 12/1996 | Burton et al. ............... 604/101 |
| 5,643,229 A | | 7/1997 | Sinaiko ...................... 604/267 |
| 5,645,528 A | * | 7/1997 | Thome |
| 5,718,678 A | * | 2/1998 | Fleming |
| 5,759,173 A | | 6/1998 | Prissman et al. ............. 604/96 |
| 5,807,349 A | * | 9/1998 | Person et al. |
| 5,971,974 A | * | 10/1999 | Keisz |

* cited by examiner

Primary Examiner—Steven D. Maki
(74) Attorney, Agent, or Firm—Lyon & Lyon LLP

(57) ABSTRACT

The invention provides a nested tubing cannula which comprises outer and inner elongate tubular members, both having a proximal end, a distal end, and a lumen therebetween. The inner tubular member is sealed at its distal end and is nested substantially coaxially within the lumen of the outer tubular member, so that the gap between the inner and the outer tubular member defines a second lumen whereas the first lumen is the lumen of the inner tubular member. A tubular sleeve is disposed coaxially between the inner and outer tubular members. A balloon is mounted on a distal region of the outer tubular member and is in communication with the first lumen. The cannula further comprises a port proximal or distal the balloon occluder and is in communication with the second lumen. Methods for making the devices herein are disclosed.

9 Claims, 3 Drawing Sheets

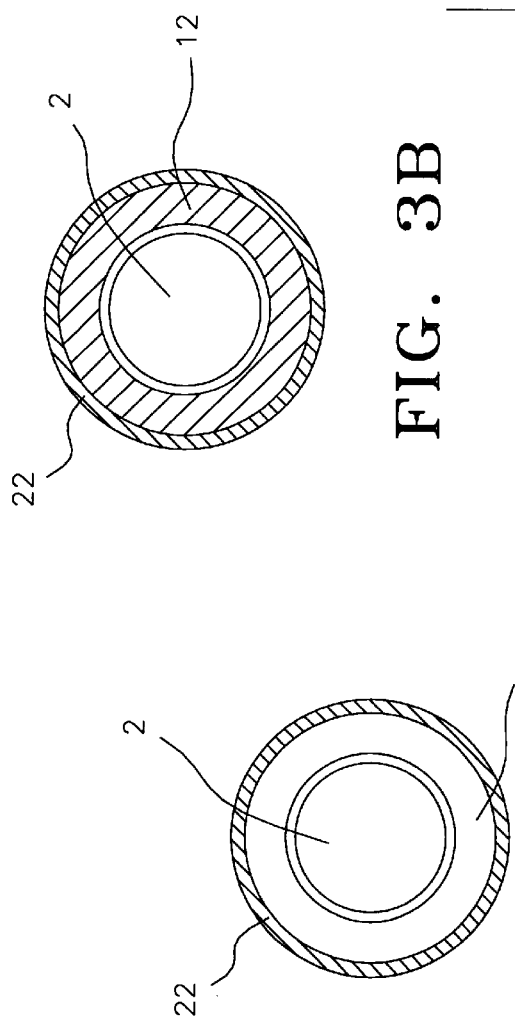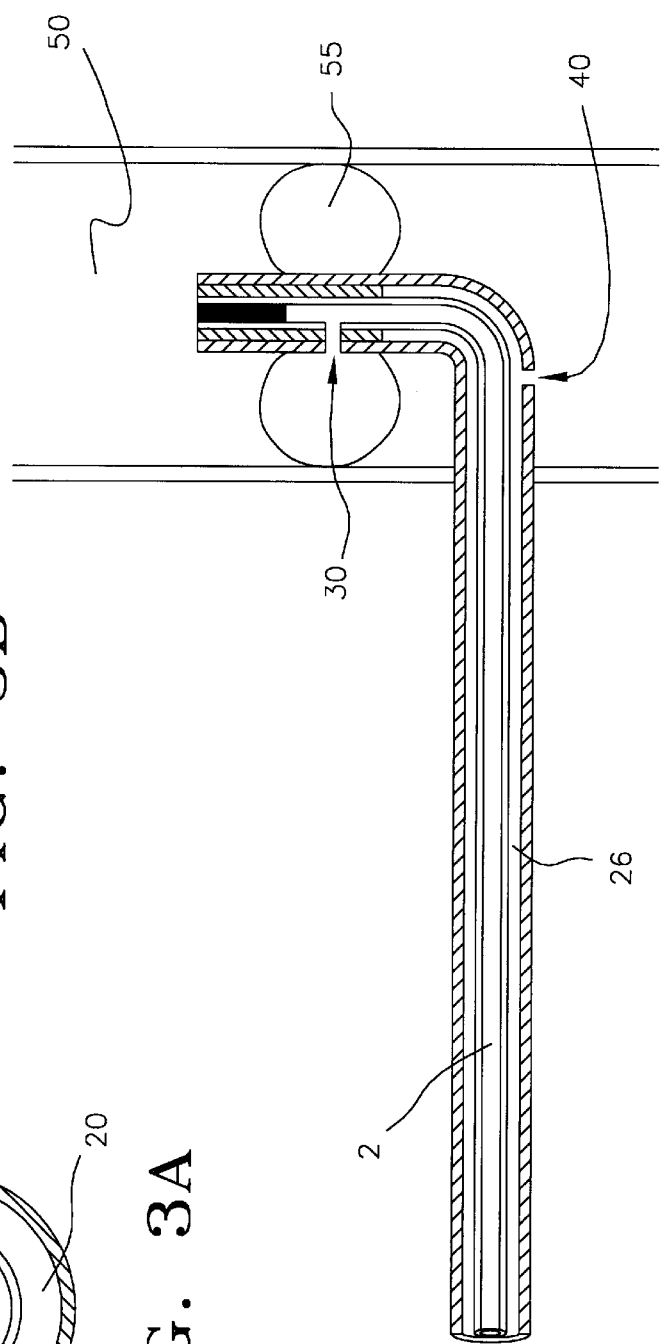

NESTED TUBING SECTIONS AND METHOD FOR MAKING

This is a division of U.S. application Ser. No. 09/131,248, filed Aug. 7, 1998, now U.S. Pat. No. 5,954,694 the contents of which are incorporated herein by reference.

FIELD OF THE INVENTION

The present invention relates to methods for making curved or straight segments of polymeric devices which comprise nested tubing of varying physical and mechanical characteristics.

BACKGROUND OF THE INVENTION

Since minimally invasive surgical procedures which use an endoscopic approach are now widely used in many surgical specialties, including cardiothoracic surgery, new surgical techniques and instruments have been developed especially to assist in minimally invasive coronary artery bypass grafting (CABG) surgeries. Devices having multiple lumens and ports can be used to deliver fluid and introduce instruments, such as pressure monitors, aspirators, or filters.

Techniques used to create a cannula or catheter having multiple lumens and shapes generally include adhesive bonding, injection or compression molding, casting and machining of devices. The traditional techniques are plagued by the following problems: (1) filling tubing with adhesives is difficult to control and inconsistent, creating yield losses and quality problems, (2) injection or compression molding requires costly tooling and cannot form specific shapes, and (3) machining is labor-intensive and cannot form certain shapes. A need therefore exists for methods which provide easy and consistent means of forming cannulas or catheters which have multi-layered tubing cross-sections, and for the resulting devices.

SUMMARY OF THE INVENTION

The present invention provides a nested tubing cannula, which has multi-layered tubing cross-sections. In minimally invasive CABG surgery, the cannula may function as a balloon occluder for aortic occlusion and a conduit for cardioplegia delivery or blood delivery from cardiopulmonary bypass (CPB) machine. The cannula comprises two elongate tubular members, which both have a proximal end, a distal end, and a lumen therebetween. One tubular member (the inner tubular member) has a diameter smaller than the other (the outer tubular member). The smaller tubular member is nested substantially coaxially within the lumen of the larger tubular member, so that the gap between the larger tubular member and the smaller tubular member defines one lumen, whereas another lumen is provided by the lumen of the smaller tubular member. A tubular sleeve may be disposed coaxially between the smaller and larger tubular members. In certain embodiments, the inner tubular member will be fitted with a beading or plug occluding and sealing the distal opening of its lumen. In an alternative embodiment, the distal end of the cannula may be angulated (e.g., at approximately 90°) relative to its proximal end for better positioning within a vessel wall.

Where the cannula comprises a balloon occluder, an elastomeric balloon with an inflatable chamber is mounted on the distal region of the outer tubular member. The chamber of the balloon communicates with the lumen of the inner tubular member by a channel which passes radially through the outer tube member, the tubular sleeve, and the inner tubular member. The cannula may have one or more ports either proximal or distal the balloon occluder and communicating with the lumen of the gap between the inner and outer tubular members.

The method for making nested tubing sections includes an initial step of heat-bonding a beading into the lumen of a tubular member which has a proximal end, a distal end, and a lumen therebetween, to seal the distal opening. A tubular sleeve is heat-bonded circumferentially about the distal end of the tubular member. The tubular member is then nested within the lumen of a larger tubular member which has a proximal end, a distal end, and a lumen therebetween. The tubular sleeve may be aligned substantially with the distal end of the outer tubular member. The outer tubular member is then heat-bonded to the tubular sleeve. A channel is created through the outer tubular member, the tubular sleeve, and inner tubular member, the channel communicating with the lumen of the inner tubular member. Another channel or channels are created through the outer tubular member and are in communication with the lumen disposed between the inner and the outer tubular members. In an alternative embodiment where the distal end of the cannula is angulated relative to its proximal end, heat is applied to bend the distal end of the cannula.

It will be understood that there are many advantages to creating nested tubing sections disclosed herein. This invention does not require expensive tooling, but simply utilizes multiple tubes that are nested together and bonded. Internal inserts may be formed into the tubes at varying layers. In addition, varying materials having different physical properties, such as hardness, flexibility, color and melting temperature, may be incorporated to improve desired performance characteristics. For example, a low melting temperature outer tube, a rigid center tube and soft inner tube can be combined to create a rigid, soft tip, heat-bondable tube.

BRIEF DESCRIPTION OF THE DRAWINGS

FIG. 3A depicts a cross-sectional view through section line A—A of the embodiment depicted in FIG. 3.

FIG. 3B depicts a cross-sectional view through section line B—B of the embodiment depicted in FIG. 3.

FIG. 5 depicts deployments of an angled cannula which has a balloon occluder and cardioplegia port inside an aorta.

DETAILED DESCRIPTION OF THE PREFERRED EMBODIMENTS

Figure 1:
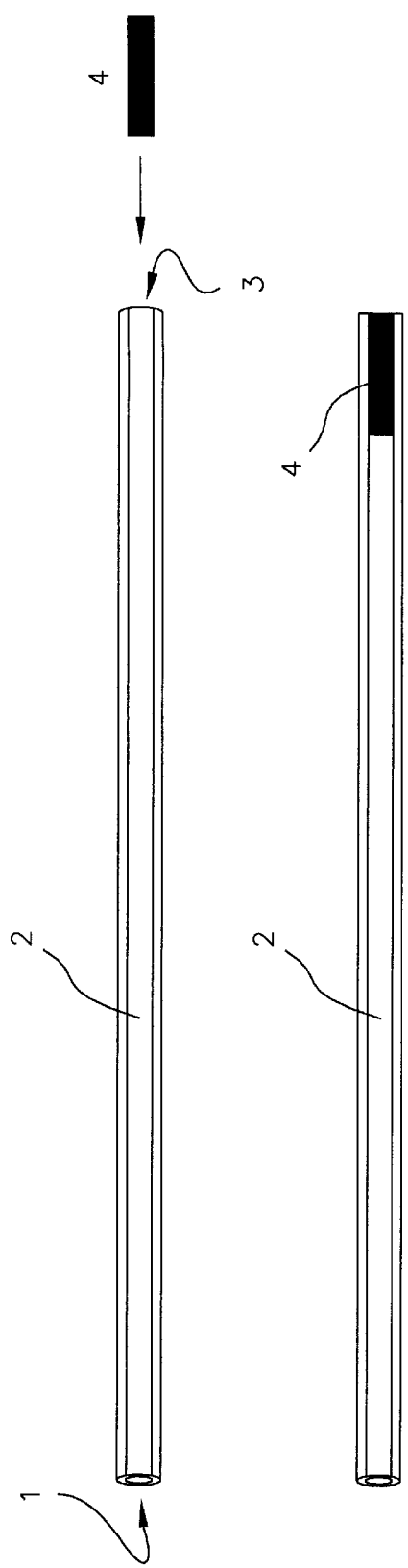
FIG. 1 depicts an elongate tubular member and a beading inserted at its distal end.

The devices and methods disclosed herein can be used in aortic cannulation for CPB during minimally invasive CABG surgery. More specifically, when a cannula with the nested tubing sections is deployed within an aorta, a balloon occluder can be inflated through its communicating lumen to provide aortic occlusion, and cardioplegia solution can be delivered through a second lumen upstream to the heart to provide cardiac arrest. FIG. 1 depicts an elongate tubular member in a beading. The tubular member has proximal end 1, distal end 3, and lumen 2. Beading 4 is inserted at distal end 3 of the tubular member to provide a seal.

Figure 2:
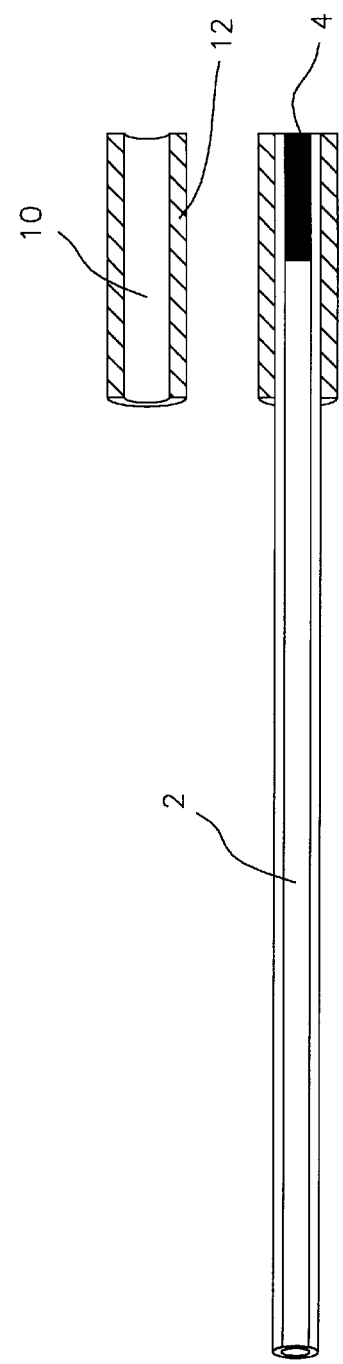
FIG. 2 depicts a tubular sleeve bonded circumferentially about the distal end of the tubular member.

FIG. 2 depicts a tubular sleeve and a sealed tubular member. Tubular sleeve 12 is bonded circumferentially about the distal end of the tubular member.

Figure 3:
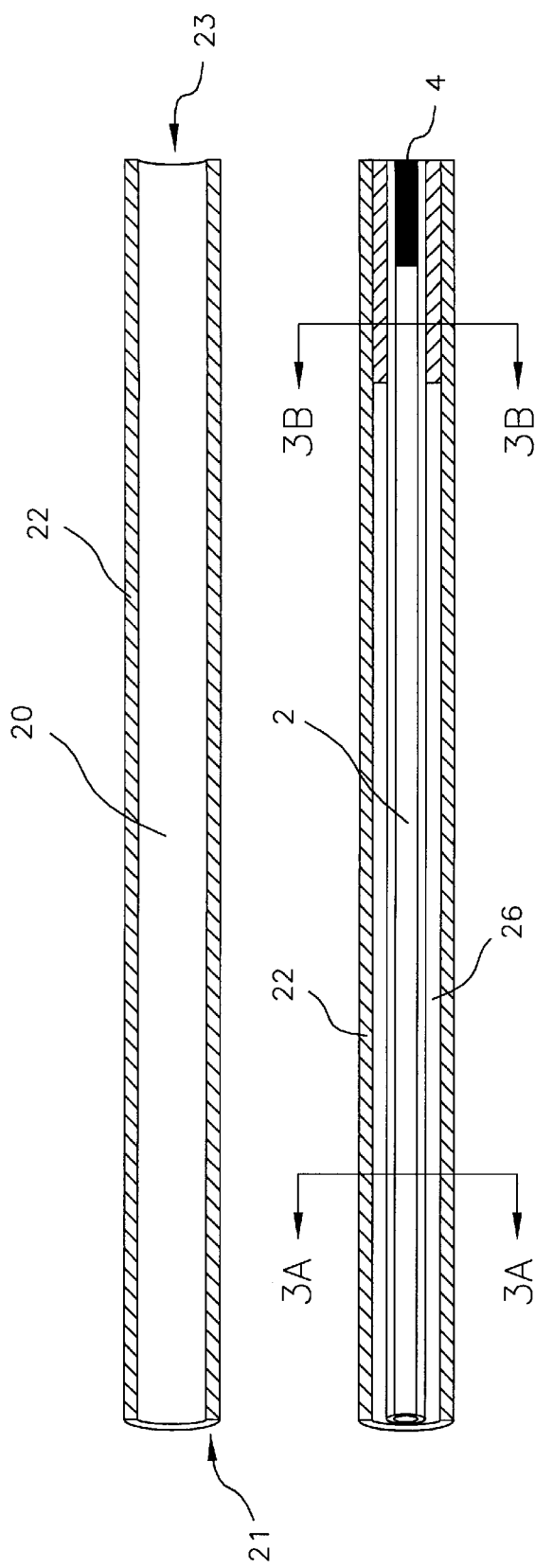
FIG. 3 depicts an outer tubular member containing the inner tubular member having a tubular sleeve bonded between the two tubular members.

FIG. 3 depicts an outer tubular member containing the inner tubular member having a tubular sleeve interposed between the two tubular members. Outer tubular member 22 has proximal end 21, distal end 23, and lumen 20. Lumen 26 is created by the gap between the inner and the outer tubular members. FIG. 3A depicts a cross-sectional view through section line A—A of the tubular member depicted in FIG. 3. FIG. 3B depicts a cross-sectional view through section B—B of the nested tubing sections depicted in FIG. 3. This embodiment has two lumens: existing lumen 2 from the inner tubular member and new lumen 26 created between the outer and inner tubular members.

Figure 4:
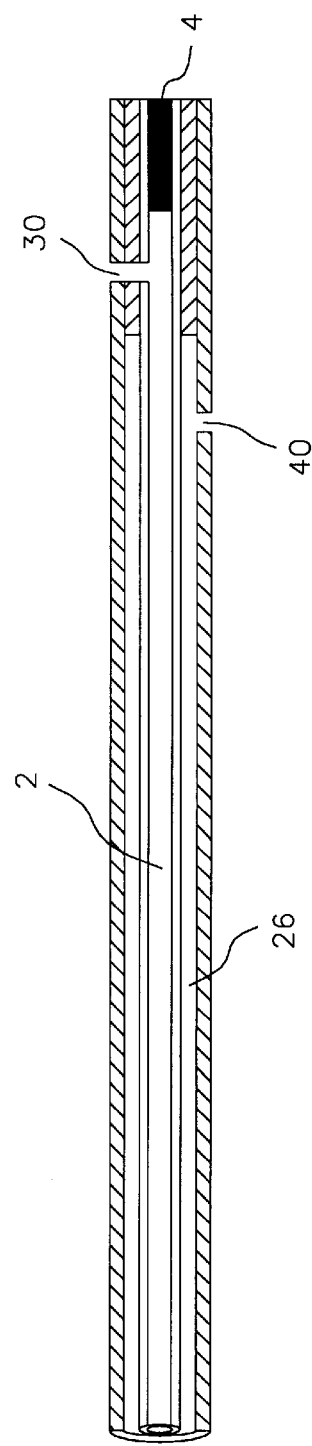
FIG. 4 depicts a cannula which has the nested tubing sections.

FIG. 4 depicts a cannula having the nested tubing sections. Port 30 is made by creating a channel through the outer tubular member, the tubular sleeve, and the inner tubular member, and is in communication with lumen 2. Port 40 is made by creating a channel through the outer tubular member distal to port 30 and is in communication with lumen 26. In an alternative embodiment, port 40 is made by creating a channel through the outer tubular member proximal to port 30.

FIG. 5 depicts an alternative embodiment of a cannula deployed inside an aorta, so that its distal end is parallel to the aortic wall. This embodiment comprises balloon occluder 55 mounted at the distal end of the cannula having balloon occluder port 30 communicating with lumen 2, and cardioplegia port 40 communicating with lumen 26. When this cannula is deployed downstream of the aorta, the balloon occluder is inflated through lumen 2 to provide aortic occlusion for CPB, and cardioplegia solution is delivered through port 40 upstream of the heart to provide cardiac arrest. When this cannula is deployed upstream the aorta, port 40 can be used to deliver oxygenated blood from the CPB machine.

Alternatively, port 40, if made proximal the balloon occluder, can deliver oxygenated blood from the CPB machine when the cannula is inserted downstream of the aorta, and can deliver cardioplegia solution to the heart when the cannula is inserted upstream of the aorta. The length of the inner tubular member and the outer tubular member will generally be between 5–50 centimeters, preferably approximately 20 centimeters. The lumenal diameter of the inner tubular member will generally be between 0.2 and 1.0 centimeters, preferably approximately 0.5 centimeters. The lumenal diameter of the outer tubular member will be between 1.0 centimeter to 3.0 centimeters, preferably approximately 2.0 centimeters. The length of the beading will generally be between 0.5 and 2.0 centimeters, preferably approximately 1.0 centimeters. The length of the tubular sleeve will generally be between 1.0 and 4.0 centimeters, preferably approximately 2.0 centimeters. The foregoing ranges are set forth solely for the purpose of illustrating typical device dimensions. The actual dimensions of a device constructed to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for making nested tubing sections, comprising the steps of:

providing an inner tubular member having a proximal end, a distal end, and a lumen therebetween;

heat-bonding a beading into the lumen of the inner tubular member to seal the distal end;

heat-bonding a tubular sleeve circumferentially about the distal end of the inner tubular member, so that the distal end of the tubular sleeve and the distal end of the inner tubular member are substantially aligned;

providing an outer tubular member having a proximal end, a distal end, and a lumen therebetween;

nesting the inner tubular member within the lumen of the outer tubular member so that the distal end of the tubular sleeve, the distal end of the inner tubular member, and the distal end of the outer tubular member are all substantially aligned with one another; and heat-bonding the outer tubular member to the tubular sleeve.

2. The method of claim 1, further comprising the step of creating a channel through the outer tubular member, the tubular sleeve, and the inner tubular member, said channel in communication with the lumen of the inner tubular member.

3. The method of claim 1, further comprising a step of creating a channel through the outer tubular member, said channel in communication with the lumen disposed between the inner and outer tubular members.

4. The method of claim 1, further comprising the step of mounting an elastomeric balloon on the distal end of the outer tubular member.

5. The method of claim 1, further comprising the step of heat bending the distal end of the inner and outer tubular members so that the distal end is angulated relative to the proximal end.

6. A method for making nested tubing sections, comprising the steps of:

providing an inner tubular member having a proximal end, a distal end, and a lumen therebetween;

heat-bonding a beading into the lumen of the inner tubular member to seal the distal end;

heat-bonding a tubular sleeve circumferentially about the distal end of the inner tubular member, so that the distal end of the tubular sleeve and the distal end of the inner tubular member are substantially aligned;

providing an outer tubular member having a proximal end, a distal end, and a lumen therebetween;

nesting the inner tubular member within the lumen of the outer tubular member so that the distal end of the tubular sleeve, the distal end of the inner tubular member, and the distal end of the outer tubular member are all substantially aligned with one another;

heat-bonding the outer tubular member to the tubular sleeve; and heat bending the distal end of the inner and outer tubular members so that an axis of the distal end is displaced at approximately a ninety degree angle relative to an axis of the proximal end.

7. The method of claim 6, further comprising the step of creating a channel through the outer tubular members the tubular sleeve, and the inner tubular member, said channel in communication with the lumen of the inner tubular member.

8. The method of claim 6, further comprising a step of creating a channel through the outer tubular member, said channel in communication with the lumen disposed between the inner and outer tubular members.

9. The method of claim 6, further comprising the step of mounting an elastomeric balloon on the distal end of the outer tubular member.

* * * * *